United States Patent [19]

Smith

[11] 4,211,878

[45] Jul. 8, 1980

[54] ALKANOLAMINE DERIVATIVES

[75] Inventor: Leslie H. Smith, Macclesfield, England

[73] Assignee: Imperial Chemical Industries Limited, London, England

[21] Appl. No.: 839,568

[22] Filed: Oct. 5, 1977

[30] Foreign Application Priority Data

Oct. 7, 1976 [GB] United Kingdom ............... 41714/76

[51] Int. Cl.$^2$ .................. C07D 333/24; C07D 307/12; A01N 9/00; A01N 9/28
[52] U.S. Cl. ......................................... 549/78; 549/64; 549/66; 549/70; 260/347.8; 424/275; 424/285
[58] Field of Search ..................... 260/332.2 A, 347.8; 549/64, 66, 70, 78

[56] References Cited

U.S. PATENT DOCUMENTS

| 3,607,859 | 9/1971 | Feder | 260/332.2 A |
| 3,639,476 | 2/1972 | Eberle et al. | 260/332.2 A |

Primary Examiner—Alan Siegel
Attorney, Agent, or Firm—Cushman, Darby & Cushman

[57] ABSTRACT

Novel 1-aryloxy-3-amidoamidoalkylamino-2-propanol derivatives, processes for their manufacture, pharmaceutical compositions containing them and methods of using them in the treatment of heart diseases. Representative of the compounds disclosed is 1-(o-cyanophenoxy)-3-β-(2-thenamidoacetamido)ethylaminopropan-2-ol.

8 Claims, No Drawings

ALKANOLAMINE DERIVATIVES

This invention relates to new alkanolamine derivatives which possess β-adrenergic blocking activity.

According to the invention there is provided a new alkanolamine derivative of the formula:

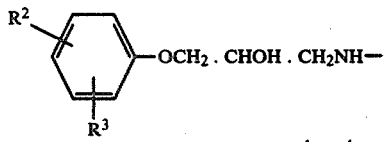

wherein $A^1$ stands for an alkylene radical of from 2 to 6 carbon atoms; wherein $A^2$ stands for a direct link of for an alkylene radical of up to 6 carbon atoms; wherein $R^1$ stands for the hydrogen atom or for an alkyl, halogenoalkyl, alkenyl or cycloalkyl radical each of up to 10 carbon atoms, or for an aryl radical of the formula:

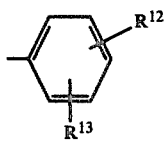

or for a heterocyclic radical; wherein $R^2$, $R^3$, $R^{12}$ and $R^{13}$, which may be the same or different, each stands for a hydrogen or halogen atom, a hydroxy, amino, nitro, carbamoyl or cyano radical, or an alkyl, alkenyl, alkoxy, alkylthio, alkenyloxy, alkanoyl or acylamino radical each of up to 6 carbon atoms, or wherein $R^2$ and $R^3$ together, and/or $R^{12}$ and $R^{13}$ together, form the trimethylene, tetramethylene or buta-1,3-dienylene radical such that together with the adjacent benzene ring they form respectively the indanyl, 5,6,7,8-tetrahydronaphthyl or naphthyl radical; wherein $X^1$ and $X^2$, which may be the same or different, each stands for an amidic linkage of the formula —NHCO—, —NHSO₂— or —CONH—; wherein $Y^1$ stands for a direct link or (except when $X^1$ is —CONH—) for the imino (—NH—) radical and wherein $Y^2$ stands for a direct link, or for an alkylene, oxyalkylene or alkyleneoxy radical each of up to 6 carbon atoms, or (except when $X^2$ is —CONH—) for the imino (—NH—) radical or for an alkylimino or imino-alkylene radical each of up to 6 carbon atoms, or (except when $R^1$ stands for the hydrogen atom) for the oxygen atom; or an acid-addition salt thereof.

It will be observed that the alkanolamine derivative of the invention possesses an asymmetric carbon atom, namely the carbon atom of the —CHOH— group in the alkanolamine side-chain, and it can therefore exist in racemic and optically-active forms. It is to be understood that this invention encompasses the racemic form of the alkanolamine derivative and any optically-active form which possesses β-adrenergic blocking activity, it being a matter of common general knowledge how a racemic compound may be resolved into optically-active forms, and how the β-adrenergic blocking activity of these forms may be determined. It is further to be understood that β-adrenergic blocking activity usually predominates in that optically-active form which has the "S" absolute configuration of the said —CHOH— group.

A suitable value for the alkylene radical $A^1$ is, for example, the ethylene, trimethylene, tetramethylene, hexamethylene, 1-methylethylene, 2-methylethylene or 1,1-dimethylethylene radical. $A^1$ is preferably the ethylene, 1-methylethylene or 1,1-dimethylethylene radical, especially the ethylene radical.

A suitable value for $A^2$ when it stands for an alkylene radical is, for example, the methylene or ethylidene radical or one of the values set out above for the alkylene radical $A^1$. $A^2$ is preferably a direct link or the methylene, ethylidene or ethylene radical, and especially is the methylene or ethylene radical.

A suitable value for $R^1$ when it stands for an alkyl, halogenoalkyl, alkenyl or cycloalkyl radical is, for example, the methyl, ethyl, n-propyl, isopropyl, n-butyl, isobutyl, t-butyl, n-pentyl, n-octyl, trifluoromethyl, allyl, cyclopropyl, cyclopentyl or cyclohexyl radical. A preferred value for $R^1$ from this group of values is the methyl, isopropyl or t-butyl radical.

A suitable value for $R^1$ when it stands for a heterocyclic radical is, for example, a 5 or 6-membered saturated or unsaturated monocyclic heterocyclic radical containing one or two heteroatoms selected from nitrogen, oxygen or sulphur atoms, which heterocyclic radical may optionally contain one or two substituents selected from alkyl and alkoxy radicals each of up to 6 carbon atoms, for example methyl, ethyl, methoxy and ethoxy radicals and, where the heterocyclic radical bears an appropriate degree of saturation, one or two oxo substituents.

A particular heterocyclic radical is, for example, a pyrrolyl, furyl, thienyl, imidazolyl, thiazolyl, pyridyl, pyrazinyl or pyridazinyl radical, for example the 2-pyrrolyl, 2-furyl, 2-thienyl, 3-thienyl, 2-imidazolyl, 2-thiazolyl, 4-pyridyl, 3-methyl-2-pyrazinyl or 2-pyridazinyl radical. A preferred heterocyclic radical $R^1$ is the 2-thienyl or 2-furyl radical.

A suitable value for $R^2$, $R^3$, $R^{12}$ or $R^{13}$ when it stands for a halogen atom is, for example, the fluroine, chlorine, bromine or iodine atom.

A suitable value for $R^2$, $R^3$, $R^{12}$ or $R^{13}$ when it stands for an alkyl, alkenyl, alkoxy, alkylthio, alkenyloxy, alkanoyl or acylamino radical is, for example, the methyl, ethyl, n-propyl, allyl, methoxy, isopropoxy, methylthio, allyloxy, formyl, acetyl or acetamido radical.

Preferably $R^2$ stands for the hydrogen or chlorine atom or the hydroxy, carbamoyl, cyano, methyl, allyl, methoxy or allyloxy radical, especially the hydrogen or chlorine atom or the cyano, methyl, methoxy or allyloxy radical, this substituent preferably being in the 2-position of the phenyl nucleus, and $R^3$ stands for the hydrogen atom, or $R^2$ and $R^3$ together with the adjacent benzene ring form the 1-naphthyl radical.

Preferably $R^{12}$ stands for the hydrogen or chlorine atom or the hydroxy or nitro radical and $R^{13}$ stands for the hydrogen atom, or $R^{12}$ and $R^{13}$ together with the adjacent benzene ring form the 1-naphthyl radical.

A suitable value for $Y^2$ when it stands for an alkylene, oxyalkylene or alkyleneoxy radical is, for example, the methylene, ethylene, oxymethylene, methyleneoxy, ethyleneoxy, trimethyleneoxy, 1-methylethylideneoxy or 1-methylpropylideneoxy radical.

A suitable value for $Y^2$ when it stands for an alkylimino or iminoalkylene radical is, for example, the methylimino or iminoethylene radical.

$X^1$ is preferably the —NHCO— or —CONH— radical, especially the —NHCO— radical, and $X^2$ is especially the —NHCO— or —CONH— radical.

$Y^1$ is especially a direct link and $Y^2$ is preferably a direct link or the methylene, oxymethylene, methyleneoxy or imino radical, or the oxygen atom, especially a direct link or the methylene radical.

A suitable acid-addition salt of an alkanolamine derivative of the invention is, for example, a salt derived from an inorganic acid, for example a hydrochloride, hydrobromide, phosphate or sulphate, or a salt derived from an organic acid, for example an oxalate, lactate, tartrate, acetate, salicylate, citrate, benzoate, β-naphthoate, adipate or 1,1-methylene-bis-(2-hydroxy-3-naphthoate), or a salt derived from an acidic synthetic resin, for example a sulphonated polystyrene resin.

One preferred alkanolamine derivative of the invention is a compound of the formula given above wherein $A^1$ stands for the ethylene radical, $A^2$ stands for a direct link or for the methylene or ethylene radical, $R^1$ stands for an alkyl radical of up to 6 carbon atoms or for a phenyl, monochlorophenyl, mononitrophenyl, monohydroxyphenyl, 1-naphthyl, 2-thienyl or 2-furyl radical, either $R^2$ stands for hydrogen or for the chloro or cyano radical, or for an alkyl, alkenyl, alkoxy or alkenyloxy radical each of up to 3 carbon atoms and $R^3$ stands for hydrogen, or $R^2$ and $R^3$ together with the adjacent benzene ring form the 1-naphthyl radical, $X^1$ stands for the —NHCO— radical, $X^2$ stands for the —NHCO— or —CONH— radical, $Y^1$ stands for a direct link and $Y^2$ stands for a direct link or for the methylene radical, or is an acid-addition salt thereof.

Specific alkanolamine derivatives of the invention are those hereinafter described in the Examples. Of these, preferred compounds by virture of their high cardioselective β-adrenergic blocking activity (as hereinafter defined) are:

1-(o-cyanophenoxy)-3-β-(2-thenamidoacetamido)ethylaminopropan-2-ol;
1-(o-cyanophenoxy)-3-β-(benzamidoacetamido)ethylaminopropan-2-ol;
1-(o-chlorophenoxy)-3-β-(phenylacetamidoacetamido)ethylaminopropan-2-ol; and
1-(o-chlorophenoxy)-3-β-(2-thenamidoacetamido)ethylaminopropan-2-ol;
and the acid-addition salts thereof.

The alkanolamine derivative of the invention may be manufactured by any chemical process known to be useful for the manufacture of chemically-analogous compounds.

A preferred process for the manufacture of an alkanolamine derivative of the invention wherein $X^1$ stands for an amidic linkage of the formula —NH—CO— comprises the reaction of a compound of the formula:

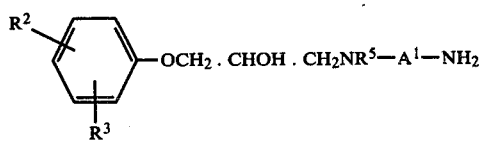

wherein $A^1$, $R^2$ and $R^3$ have the meanings stated above and wherein $R^5$ stands for hydrogen or for the benzyl radical, with a compound of the formula:

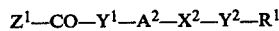

$$Z^1\text{—CO—}Y^1\text{—}A^2\text{—}X^2\text{—}Y^2\text{—}R^1$$

wherein $A^2$, $R^1$, $X^2$, $Y^1$ and $Y^2$ have the meanings stated above, and wherein $Z^1$ stands for a displaceable radical, whereafter if $R^5$ stands for the benzyl radical this radical is removed by hydrogenolysis.

The displaceable radical $Z^1$ may be, for example, a halogen atom, for example the chlorine or bromine atom, or a sulphonyloxy radical, for example an alkanesulphonyloxy radical of up to 6 carbon atoms or an arenesulphonyloxy radical of up to 10 carbon atoms, for example the methanesulphonyloxy, benzene-sulphonyloxy or toluene-p-sulphonyloxy radical, or an alkoxy, alkoxycarbonyl or aryloxy radical of up to 10 carbon atoms, for example the methoxy, ethoxy, ethoxycarbonyl, phenoxy or 2,4,5-trichlorophenoxy radical. Alternatively, $Z^1$ may be the hydroxy radical, in which case the reaction is carried out in the presence of a condensing agent, for example a carbodi-imide.

When $Y^1$ in the final product is the imino radical, an isocyanate of the formula $$\text{OCN—}A^2\text{—}X^2\text{—}Y^2\text{—}R^1$$

wherein $A^2$, $R^1$ $X^2$ and $Y^2$ have the meanings stated above, may be used to react with the amine.

A compound wherein $X^1$ stands for an amidic linkage of the formula —CONH— may be obtained by the reaction of a compound of the formula

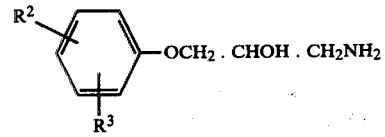

wherein $R^2$ and $R^3$ have the meanings stated above with a compound of the formula

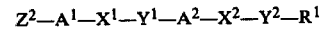

$$Z^2\text{—}A^1\text{—}X^1\text{—}Y^1\text{—}A^2\text{—}X^2\text{—}Y^2\text{—}R^1$$

wherein $A^1$, $A^2$, $R^1$, $X^1$, $X^2$, $Y^1$ and $Y^2$ have the meanings stated above and wherein $Z^2$ stands for a displaceable halogen or sulphonyloxy radical as defined above for $Z^1$.

A compound wherein one or more of $R^2$, $R^3$, $R^{12}$ and $R^{13}$ stands for the hydroxy radical may be obtained by the hydrogenolysis of the corresponding compound wherein one or more of $R^2$, $R^3$, $R^{12}$ and $R^{13}$ stands for the benzyloxy radical.

Optically-active enantiomorphs of the alkanolamine derivative of the invention may be obtained by the resolution by conventional means of the corresponding racemic alkanolamine derivative of the invention.

The said resolution may be carried out by reacting the racemic alkanolamine derivative with an optically-active acid, followed by fractional crystallisation of the diastereoisomeric mixture of salts thus obtained from a diluent or solvent, for example ethanol, whereafter the optically-active alkanolamine derivative is liberated from the salt by treatment with a base. A suitable optically-active acid is, for example, (+)- or (−)-O,O-di-p-toluoyltartaric acid or (−)-2,3:4,5-di-O-isopropylidene-2-keto-L-gulonic acid.

The resolution process may be facilitated by treating the partially resolved alkanolamine derivative in free base form obtained after a single fractional crystallisation of the diastereoisomeric mixture of salts with a solubilising agent, for example a primary amine, for example allylamine, in a relatively non-polar diluent or solvent, for example petroleum ether.

The alkanolamine derivative of the invention in free base form may be converted into an acid-addition salt thereof by reaction with an acid by conventional means.

As stated above, the alkanolamine derivative of the invention or an acid-addition salt thereof possesses β-adrenergic blocking activity, and furthermore this activity is cardio-selective. This activity may be determined by the reversal of isoprenaline-induced tachycardia in rats or cats, a standard test for the determination of β-adrenergic blocking activity, and by relative freedom from antagonism of isoprenaline-induced vasodilation in cats or of the relief produced by isoprenaline of histamine-induced bronchospasm in guinea-pigs. Compounds exhibiting this cardioselective action show a greater degree of specificity in blocking the cardiac β-receptors than the β-receptors in peripheral blood vessels and bronchial muscle. Thus, a dose may be selected for such a compound at which the compound blocks the cardiac inotropic and chronotropic actions of a catecholamine such as isoprenaline but does not block the relaxation of tracheal smooth muscle produced by isoprenaline or the peripheral vasodilator action of isoprenaline. Because of this selective action, one of these compounds may advantageously be used together with a sympathomimetic bronchodilator, for example isoprenaline, orciprenaline, adrenaline or ephedrine, in the treatment of asthma and other obstructive airways diseases, inasmuch as the cardioselective compound will substantially inhibit the unwanted stimulatory effects of the bronchodilator on the heart but will not hinder the desirable therapeutic effect of the bronchodilator. A preferred alkanolamine derivative of the invention is up to ten times more active as a cardioselective β-adrenergic blocking agent than practolol. At doses of an alkanolamine derivative of the invention which produce effective β-adrenergic blockade in rats or cats, no symptoms of toxicity are apparent.

The alkanolamine derivative of the invention may be administered to warm-blooded animals, including man, in the form of a pharmaceutical composition comprising as active ingredient at least one alkanolamine derivative of the invention, or an acid-addition salt thereof, in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the alkanolamine derivative of the invention, one or more drugs selected from sedatives, for example phenobarbitone, meprobamate, chlorpromazine and the benzodiazepine sedative drugs, for example chlordiazepoxide and diazepam; vasodilators, for example glyceryl trinitrate, pentaerythritol tetranitrate and isosorbide dinitrate; diuretics, for example chlorothiazide; hypotensive agents, for example reserpine, bethanidine and guanethidine; cardiac membrane stabilising agents, for example quinidine; agents used in the treatment of Parkinson's disease and other tremors, for example benzhexol; cardiotonic agents, for example digitalis preparations; α-adrenergic blocking agents, for example phentolamine and sympathomimetic bronchodilators, for example isoprenaline, orciprenaline, adrenaline and ephedrine.

When used for the treatment of heart diseases, for example angina pectoris and cardiac arrhythmias, or for the treatment of hypertension or anxiety states in man, it is expected that the alkanolamine derivative would be given to man at a total oral dose of between 20 mg. and 600 mg. daily, at doses spaced at 6–8 hourly intervals, or at an intravenous dose of between 1 mg. and 20 mg.

Preferred oral dosage forms are tablets or capsules containing between 10 and 100 mg., and preferably 10 mg. or 50 mg. of active ingredient. Preferred intravenous dosage forms are sterile aqueous solutions of the alkanolamine derivative or of a non-toxic acid-addition salt thereof, containing between 0.05% and 1% w/v of active ingredient, and more particularly containing 0.1% w/v of active ingredient.

The invention is illustrated but not limited by the following Examples:

EXAMPLE 1

N,N'-Dicyclohexylcarbodiimide (2.5 g.) is added to a mixture of N-benzoylglycine (1.79 g.), 2,4,5-trichlorophenol (2.2 g.) and dioxan (100 ml.) and the mixture is stirred at laboratory temperature for one hour and then filtered. The filtrate is added to a solution of 1-(o-cyanophenoxy)-3-(β-aminoethyl)aminopropan-2-ol (2.35 g.) in dioxan (50 ml.), and the mixture is kept at room temperature for 1 hour and then evaporated to dryness under reduced pressure. The residue is shaken with aqueous N-acetic acid (50 ml.) and ethyl acetate (50 ml.) and the aqueous layer is separated and stirred for 5 minutes with a mixture of aqueous 2 N-sodium hydroxide (30 ml.) and diethyl ether (50 ml.). The mixture is filtered and the solid residue is crystallised from acetonitrile. There is thus obtained 1-(o-cyanophenoxy)-3-β-(benzamido-acetamido)-ethylaminopropan-2-ol, m.p. 143°–144° C.

The process described above is repeated except that the appropriate 1-phenoxy-3-(β-aminoethyl)aminopropan-2-ol derivative is used in place of the o-cyanophenoxy derivative. There are thus obtained the compounds shown in the following table:

| $R^2$ | m.p.(°C.) | Crystallisation solvent |
|---|---|---|
| H | 139–140 | acetonitrile |
| chloro | 137–138 | acetonitrile |
| methyl | 113–115 | ethyl acetate |

EXAMPLE 2

Ethyl chloroformate (0.54 g.) is added dropwise to a stirred mixture of N-acetylglycine (0.59 g.), tetrahydrofuran (40 ml.) and triethylamine (1 ml.) which is maintained at a temperature of between −15° C. and −10° C., and after the addition is complete the mixture is stirred at −10° C. for 15 minutes. A solution of 1-(o-chlorophenoxy)-3-(β-aminoethyl)aminopropan-2-ol (1.23 g.) in tetrahydrofuran (20 ml.) is then added and the mixture is allowed to warm up to laboratory temperature, stirred a further two hours and then evaporated to dryness under reduced pressure. The residue is dissolved in water (30 ml.), aqueous 2 N-sodium hydroxide solution (5 ml.) is added and the mixture is extracted three times with chloroform (30 ml. each time). The combined chloroform extracts are dried over anhydrous magnesium sulphate and evaporated to dryness under reduced pressure and the residue is crystallised from ethyl acetate. There is thus obtained 1-(o-chlorophenoxy)-3-β-(acetamidoacetamido)ethylaminopropan-2-ol, m.p. 107°-109° C.

The process described above is repeated except that an N-benzyloxycarbonamidoalkanoic acid is used as starting material in place of N-acetylglycine, and that the appropriate 1-(substituted-phenoxy)-3-(β-aminoethylamino) propan-2-ol is used as starting material. There are thus obtained the compounds described in the following table:

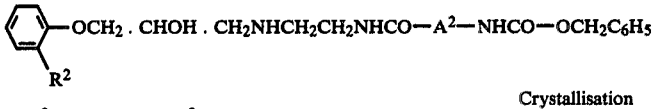

| R² | A² | m.p.(°C.) | Crystallisation solvent |
| --- | --- | --- | --- |
| cyano | —CH₂— | 97-99 | ethyl acetate |
| methyl | —CH₂— | hydrogen oxalate monohydrate 195-197 | water |
| methyl | —CH(CH₃)— | 126-130 | ethyl acetate |

EXAMPLE 3

Ethyl oxamate (0.59 g.) is added to a solution of 1-(o-cyanophenoxy)-3-(β-aminoethyl)aminopropan-2-ol (1.3 g.) in acetonitrile (20 ml.) and the solution is stirred at laboratory temperature for 16 hours, and then filtered. The residue is crystallised from ethanol and there is thus obtained 1-(o-cyanophenoxy)-3-(β-oxamoylethyl)aminopropan-2-ol, m.p. 138°-140° C.

The process described above is repeated except that ethyl N-benzyloxamate and either 1-phenoxy- or 1-(o-cyanophenoxy)-3-(β-aminoethyl)aminopropan-2-ol are used as starting materials. There are thus obtained, respectively, 1-phenoxy-3-(β-N-benzyloxamoylethyl)aminopropan-2-ol, m.p. 161°-162° C. after crystallisation from a mixture of methanol and acetonitrile, and 1-(o-cyanophenoxy)-3-(β-N-benzyloxamoylethyl)-aminopropan-2-ol, m.p. 137°-139° C. after crystallisation from a mixture of methanol and acetonitrile.

EXAMPLE 4

A mixture of N-phenylacetyl-glycine methyl ester (1.03 g.) and 1-(o-chlorophenoxy)-3-(β-aminoethyl)aminopropan-2-ol (1.23 g.) is heated at 90° C. for 16 hours and then cooled, and the residue is crystallised from acetonitrile. There is thus obtained 1-(o-chlorophenoxy)-3-β-(phenylacetamido-acetamido)ethylaminopropan-2-ol, m.p. 140°-142° C.

The process described above is repeated except that 1-(o-carbamoylphenoxy)-3-(β-aminoethyl)aminopropan-2-ol is used as starting material in place of the corresponding o-cyano compound. There is thus obtained 1-(o-carbamoylphenoxy)-3-β-(phenylacetamidoacetamido)ethylaminopropan-2-ol, m.p. 104°-106° C. after crystallisation from acetonitrile.

The process described above is repeated except that 1-(o-methoxyphenoxy)-3-(β-aminoethyl)aminopropan-2-ol and methyl N-benzylmalonamate are used as starting materials. There is thus obtained 1-(o-methoxyphenoxy)-3-(β-N-benzylmalonamoylmethyl)aminopropan-2-ol, m.p. 121°-123° C. after crystallisation from acetonitrile.

EXAMPLE 5

A mixture of 2,4,5-trichlorophenyl β-(t-butoxycarbonamido)propionate (3.7 g.), 1-o-tolyloxy-3-(β-aminoethyl)aminopropan-2-ol (2.2 g.) and tetrahydrofuran (40 ml.) is stirred at laboratory temperature for 3 hours and then evaporated to dryness. A solution of the residue in ethyl acetate (50 ml.) is added to a solution of oxalic acid (1.26 g.) in ethyl acetate (30 ml.) and the mixture is filtered. The residue is crystallised from water and there is thus obtained 1-(o-tolyloxy)-3-β-(β-t-butoxycarbonamidopropionamido)ethylaminopropan-2-ol hydrogen oxalate, m.p. 155°-157° C.

EXAMPLE 6

A mixture of N-phenoxyacetylglycine methyl ester (1.1 g.) and 1-(o-cyanophenoxy)-3-(β-amino-ethyl)aminopropan-2-ol (1.3 g.) is heated at 90° C. for 16 hours. Aqueous N-acetic acid (50 ml.) is added to the mixture and the mixture is filtered. The filtrate is added to aqueous 2 N-sodium hydroxide solution (50 ml.) and the mixture is filtered. The residue is crystallised from ethyl acetate and there is thus obtained 1-(o-cyanophenoxy)-3-β-(phenoxyacetamidoacetamido)ethylaminopropan-2-ol, m.p. 105°-106° C.

The process described above is repeated except that the appropriate N-acylglycine methyl ester and the appropriate 1-phenoxy-3-(β-aminoethyl)aminopropan-2-ol are used as starting materials. There are thus obtained the compounds shown in the following table:

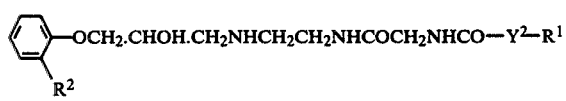

| R² | Y² | R¹ | m.p.(°C.) | Crystallisation solvent |
| --- | --- | --- | --- | --- |
| cyano | — | 2-thienyl | 147-148 | acetonitrile |
| chloro | — | 2-thienyl | 135-136 | acetonitrile |
| methyl | — | 2-thienyl | 89-91 | ethyl acetate |
| H | — | 2-thienyl | 93-95 | ethyl acetate |
| cyano | —CH₂— | phenyl | 109-110 | acetonitrile |
| carbamoyl | —CH₂O— | phenyl | 134-135 | 5% methanol in acetonitrile |

The N-2-thenoylglycine methyl ester used as starting material may be obtained as follows:

2-Thenoylchloride (7.3 g.) is added dropwise to a stirred solution of glycine methyl ester hydrochloride (6.3 g.) and sodium hydrogen carbonate (8.4 g.) in water (100 ml.) which is maintained at 5° C. The mixture is filtered and the residue is crystallised from a mixture of ethyl acetate and petroleum ether (b.p. 60°-80° C.). There is thus obtained N-2-thenoyl-glycine methyl ester, m.p. 91°-92° C.

EXAMPLE 7

A mixture of 1-phenoxy-3-(N-benzyl-N-β-aminoethyl)aminopropan-2-ol (10 g.), succinic anhydride (3.34 g.) and toluene (50 ml.) is kept at laboratory temperature for 17 hours and then evaporated to dryness under reduced pressure. The residue is dissolved in ethanol (50 ml.), 30% palladium-on-charcoal catalyst (0.5 g.) is added and the mixture is shaken with hydrogen at laboratory temperature and atmospheric pressure until 700 ml. of hydrogen have been absorbed. The mixture is diluted with hot water (10 ml.), filtered and evaporated to dryness under reduced pressure. The oily residue is stirred with ethanol, the mixture is filtered and there is thus obtained as crystalline residue 1-phenoxy-3-β-(3-carboxypropionamido)-ethylaminopropan-2-ol, m.p. 159° C.

A mixture of the above compound (15.8 g.), water (40 ml.) and aqueous 40% formalin solution (5.1 ml.) is stirred at laboratory temperature for 2 hours and then evaporated to dryness under reduced pressure. The oily oxazolidine thus obtained is dissolved in aceonitrile (100 ml.), 2,4,5-trichlorophenol trichlorophenol (10.7 g.) and N,N'-dicyclohexylcarbodi-imide (11.5 g.) are added and the mixture is stirred for 1 hour at laboratory temperature and then filtered. The filtrate is diluted with water and extracted with ethyl acetate, and the extract is washed with water, dried and evaporated to dryness under reduced pressure.

A solution of the oily trichlorophenyl ester thus obtained (5.03 g.) and 3-phenylpropylamine (1.35 g.) in acetonitrile (10 ml.) is stirred at laboratory temperature for 1 hour, diluted with water and extracted with ethyl acetate. The extract is washed with aqueous 2 N-sodium hydroxide solution and then with water, dried and evaporated to dryness under reduced pressure. The residue is dissolved in ethanol, an excess of a saturated ethereal solution of oxalic acid is added and the mixture is filtered. The solid residue is crystallised from isopropanol and there is thus obtained 1-phenoxy-3-β-[2-(N-3-phenylpropylcarbamoyl) propionamido]-ethylaminopropan-2-ol hydrogen oxalate monohydrate, m.p., 105°–106° C.

EXAMPLE 8

Benzoyl isocyanate (1.5 g.) is added to a solution of 1-p-benzyloxyphenoxy-3-(N-benzyl-N-β-aminoethyl)aminopropan-2-ol (4.06 g.) in dioxan (30 ml.). The mixture is evaporated to dryness under reduced pressure, the residue is dissolved in acetic acid (50 ml.) and the solution is shaken with hydrogen in the presence of a 30% palladium-on-charcoal catalyst at laboratory temperature and atmospheric pressure until 400 ml. of hydrogen have been absorbed. The mixture is filtered, the filtrate is evaporated to dryness under reduced pressure and the residue is crystallised from ethanol. There is thus obtained 1-p-hydroxyphenyl-3-β-(3-benzoylureido)ethylaminopropan-2-ol, m.p. 152°–154° C.

EXAMPLE 9

The process described in Example 8 is repeated except that corresponding 1-o-tolyloxy derivative is used as starting material in place of the 1-p-benzyloxyphenoxy derivative. The crude reaction product before hydrogenation is purified by chromatography on a silica gel column using a 1:1 v/v mixture of ethyl acetate and toluene as eluant. The crude reaction product after hydrogenation is dissolved in ethanol, ethanolic hydrogen chloride solution is added and the mixture is filtered. There is thus obtained 1-o-tolyloxy-3-β-(3-benzoylureido)ethylaminopropan-2-ol hydrochloride, m.p. 192°–194° C.

EXAMPLE 10

The process described in Example 6 is repeated except that the appropriate N-acylglycine methyl or ethyl ester and the appropriate 1-phenoxy-3-(β-aminoethyl)aminopropan-2-ol are used as starting materials. There are thus obtained the compounds shown in the following table:

$$\text{\begin{tabular}{c} \\ \end{tabular}} \text{—OCH}_2 . \text{CHOH} . \text{CH}_2\text{NHCH}_2\text{CH}_2\text{NHCOCH}_2\text{NHCO—R}^1$$

with $R^2$ on the ring

| $R^2$ | $R^1$ | m.p.(°C.) | Crystallisation solvent |
|---|---|---|---|
| cyano | 2-furyl | 128–130 | acetonitrile |
| methyl | p-chlorophenyl | 134–136 | acetonitrile |
| methyl | o-chlorophenyl | oxalate hemihydrate 181–183 | ethanol |
| methyl | m-chlorophenyl | 133–135 | ethyl acetate |
| methyl | o-nitrophenyl | 129–131 | acetonitrile |
| allyl | p-chlorophenyl | 117–119 | ethyl acetate |
| allyloxy | p-chlorophenyl | 134–136 | acetonitrile |
| methoxy | 2-thienyl | hydrogen oxalate 163–165 | ethanol |

The process described above is repeated using the appropriate 1-aryloxy-3-(β-aminoethyl)aminopropan-2-ol and the appropriate ethyl ester and there are thus obtained the compounds shown in the following table:

| Aryl—OCH$_2$ . CHOH . CH$_2$NHCH$_2$CH$_2$NHCO—A$^2$—X$^2$—Y$^2$—R$^1$ | | | | |
|---|---|---|---|---|
| Aryl | —A$^2$—X$^2$—Y$^2$— | R$^1$ | m.p.(°C.) | Crystallisation solvent |
| o-tolyl | —CH$_2$NHSO$_2$— | phenyl | hydrogen oxalate 144–146 | acetonitrile* |
| 1-naphthyl | —CH$_2$NHCO— | 1-naphthyl | 133–135 | acetonitrile* |
| 1-naphthyl | —CH$_2$NHCO— | 2-thienyl | 80–82 | acetonitrile |
| o-tolyl | —CH$_2$CH$_2$NHCOCH$_2$— | phenyl | 127–128 | acetonitrile |
| o-tolyl | —CH$_2$CH$_2$NHCO— | phenyl | 127–128 | acetonitrile |
| o-tolyl | —CH$_2$CH$_2$NHCONH— | phenyl | 121–123 | ethyl acetate/ acetonitrile |
| phenyl | —CH$_2$CONH— | p-hydroxyphenyl | 183–185 | ethanol* |
| o-cyanophenyl | —CH$_2$CONHCH$_2$— | 2-furyl | 111–113 | ethyl acetate |

*Initial purification before crystallisation by chromatography on a silica gel column using a 60:20:10:35 v/v mixture of toluene/ethyl acetate/concentrated aqueous ammonium hydroxide solution/ethanol as eluant.

The various ester used as starting materials may be obtained by a similar process to that described in the last paragraph of Example 6. N-o-Chlorobenzoylglycine ethyl ester has m.p. 66°-68° C. and N-m-chlorobenzoylglycine ethyl ester has m.p. 62°-63° C. (both after crystallisation from petroleum ether b.p. 60°-80° C.).

Ethyl N-(2-furfuryl)carbamoylacetate, b.p. 150°-155° C./2.5 mm.Hg., may be obtained by heating a mixture of diethyl malonate (48.0 g.) and 2-furfurylamine (9.7 g.) at 90° C. for 48 hours.

EXAMPLE 11

A mixture of 1-(o-chlorophenoxy)-3-(β-aminoethyl) aminopropan-2-ol (1.45 g.), phenyl N-(β-isobutyramidoethyl)carbamate (1.25 g.) and dioxan (30 ml.) is heated at 90° C. for 3 hours and then cooled and filtered. The solid residue is crystallised from acetonitrile and there is thus obtained 1-(o-chlorophenoxy)-3-β-[3-(β-isobutyramidoethyl)ureido] ethylaminopropan-2-ol, m.p. 139°-140° C.

The process described above is repeated except that phenyl N-β-(3-phenylureido)ethylcarbamate and either 1-(o-tolyloxy)- or 1-(o-cyanophenoxy)-3-(β-aminoethyl) aminopropan-2-ol are used as starting materials. There are thus obtained 1-(o-tolyloxy)-3-β-[3-β-(3-phenylureido)ethyl ureido]ethylaminopropan-2-ol, m.p. 140°-143° C. after crystallisation from acetonitrile and 1-(o-cyanophenoxy)-3-β-[3-β-(3-phenylureido)ethyl-ureido]ethylaminopropan-2-ol, m.p. 152°-154° C. after crystallisation from ethanol.

The phenyl carbamates used as starting material may be obtained by the reaction of phenyl chloroformate with the appropriate β-amidoethylamine. Phenyl N-(β-isobutyramidoethyl)carbamate has m.p. 150°-152° C. after crystallisation from ethyl acetate, and phenyl N-β-(3-phenylureido)ethylcarbamate has m.p. 147°-149° C. after crystallisation from ethanol.

The various 1-aryloxy 3-(β-aminoethyl)aminopropan-2-ols used as starting materials in Examples 1 to 6, 10 and 11 may be obtained as exemplified by the following procedure:

1-(o-Carbamoylphenoxy)-2,3-epoxypropane (20 g.) is added to ethylenediamine (125 ml.) and the mixture is stirred at laboratory temperature for 1 hour and then evaporated to dryness under reduced pressure. The residue is stirred with water (150 ml.), the mixture is filtered and the filtrate is evaporated to dryness under reduced pressure. The residue is crystallised from acetonitrile and there is thus obtained as residue 1-(o-carbamoylphenoxy)-3-(β-aminoethyl) aminopropan-2-ol, m.p. 91°-93° C.

Other compounds of this type may be obtained by a similar procedure using the appropriate 1-aryloxy-2,3-epoxy-propane as starting material. Those compounds which have been characterised are described in the following table:

| 1-phenoxy derivative | m.p. of dihydrochloride | Crystallisation solvent |
| --- | --- | --- |
| 1-phenoxy | 171-172 | ethanol |
| 1-(o-tolyloxy) | 181 | ethanol |
| 1-(o-chlorophenoxy) | 208 | aqueous ethanol |
| 1-(o-cyanophenoxy) | 235-236 | aqueous ethanol |
| 1-(o-methoxyphenoxy) | 75-76 (free base) | toluene |
| 1-(o-allyloxyphenoxy) | 174-175(d) (oxalate) | aqueous ethanol |
| 1-(o-allylphenoxy) | 206-209 [di(hydrogen oxalate)] | aqueous ethanol |
| 1-(naphth-1-yloxy) | 313-315 | ethanol |

EXAMPLE 12

A mixture of 1-(p-benzyloxyphenoxy)-3-N-benzyl-N-β-aminoethyl)aminopropan-2-ol (3.9 g.) and ethyl β-phenylacetamidopropionate (2.3 g.) is heated at 90° C. for 48 hours, cooled and then dissolved in a mixture of ethanol (50 ml.) and aqueous 11-N hydrochloric acid (5 ml.). The solution is shaken with hydrogen in the presence of a 30% palladium-on-charcoal catalyst at laboratory temperature and atmospheric pressure until 610 ml. of hydrogen have been absorbed. The mixture is filtered and the filtrate is evaporated to dryness under reduced pressure. The residue is purified by chromatography in a silica gel column using a 60:20:10:35 v/v mixture of toluene/ethyl acetate/concentrated aqueous ammonium hydroxide solution/ethanol as eluant. The fraction with an $R_f$ value of 0.17 on silica gel plates using the same solvent system is collected and evaporated to dryness and the residue is crystallised from a 25:2 v/v mixture of acetonitrile and ethanol. There is thus obtained 1-(p-hydroxyphenoxy)-3-β-(β-phenylacetamidopropionamido)ethylamino-2-propanol, m.p. 137°-139° C.

EXAMPLE 13

A mixture of 1-(o-tolyloxy)-3-aminopropan-2-ol (3.6 g.), [2-(β-chloropropionamido)acet]anilide (2.4 g) and isopropanol (50 ml.) is heated at 90° C. for 18 hours and then evaporated to dryness under reduced pressure. The residue is purified by chromatography on a silica gel column using a 60:20:10:35 v/v mixture of toluene/ethyl acetate/concentrated aqueous ammonium hydroxide solution/ethanol as eluant. The fraction with an $R_f$ value of 0.45 on silica gel plates using the same solvent system is collected and evaporated to dryness and the residue is crystallised from ethanol. There is thus obtained 1-(o-tolyloxy)-3-[β-N-(N-phenylcarbamoylmethyl)carbamoyl]ethylamino-2-propanol, m.p. 160°-162° C.

The [2-(β-chloropropionamido)acet]anilide used as starting material may be obtained as follows:

β-Chloropropionyl chloride (7.0 ml.) is added dropwise during 30 minutes to a solution of (2-aminoacet-)anilide (12.43 g.), sodium bicarbonate (12.33 g.), water (100 ml.) and ethanol (100 ml.) which is stirred at 0° C., and the mixture is stirred for a further 1.5 hours and then filtered. The filtrate is evaporated to dryness under reduced pressure and the residue is dissolved in water (50 ml.). The mixture is filtered and the filtrate is extracted three times with 75 ml. of ethyl acetate each time. The combined ethyl acetate extracts are dried over anhydrous magnesium sulphate and evaporated to dryness under reduced pressure. The residue is crystallised from methanol and there is thus obtained [2-(β-chloropropionamido)acet]anilide, m.p. 173°-175° C.

What we claim is:

1. An alkanolamine derivative selected from the group consisting of a compound of the formula:

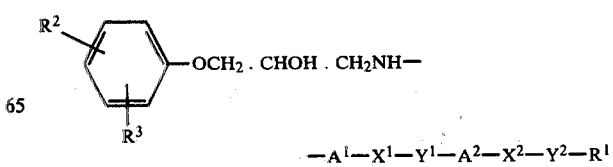

wherein $A^1$ is alkylene of from 2 to 6 carbon atoms; wherein $A^2$ is a direct link or alkylene of up to 6 carbon atoms; wherein $R^1$ is thienyl or furyl unsubstituted or contains one or two substituents selected from alkyl and alkoxy each of up to 6 carbon atoms and, where the heterocyclic bears an appropriate degree of saturation, one or two oxo substituents; wherein $R^2$ and $R^3$, which may be the same or different, each is hydrogen, halogen, hydroxy, amino, nitro, carbamoyl, cyano or alkyl, alkenyl, alkoxy, alkylthio, alkenyloxy, alkanoyl or acrylamino each of up to 6 carbon atoms, or wherein $R^2$ and $R^3$ together form trimethylene, tetramethylene or buta-1,3-dienylene such that together with the adjacent benzene ring they form respectively indanyl, 5,6,7,8-tetrahydronaphthyl or naphthyl; wherein $X^1$ and $X^2$, each is amidic of the formula —NHCO—; wherein $Y^1$ is a direct link and wherein $Y^2$ is a direct link, or alkylene, oxyalkylene or alkyleneoxy each of up to 6 carbon atoms, or oxygen; and the non-toxic pharmaceutically-acceptable acid-addition salts thereof.

2. An alkanolamine derivative as claimed in claim 1 selected from the group consisting of a compound of the formula given in claim 1 wherein $A^1$ is ethylene, trimethylene, tetramethylene, hexamethylene, 1-methylethylene, 2-methylethylene or 1,1-dimethylethylene; wherein $A^2$ is methylene, ethylene, trimethylene, tetramethylene, hexamethylene, 1-methylethylene, 2-methylethylene, 1,1-dimethylethylene or ethylidene; wherein $R^1$ is, 2-furyl, 2-thienyl or 3-thienyl, ; wherein $R^2$ and $R^3$, which may be the same or different, each is hydrogen, fluorine, chlorine, bromine, iodine, hydroxy, amino, nitro, carbamoyl, cyano, methyl, ethyl, n-propyl, allyl, methoxy, isopropoxy, methylthio, allyloxy, formyl, acetyl or acetamido, or wherein $R^2$ and $R^3$ together, form trimethylene, tetramethylene or buta-1,3-dienylene; wherein $X^1$, $X^2$ and $Y^1$ have the meanings stated in claim 1 and wherein $Y^2$ is a direct link or methylene, ethylene, oxymethylene, methyleneoxy, ethyleneoxy, trimethyleneoxy, 1-methylethylideneoxy or 1-methylpropylideneoxy, or oxygen; and the non-toxic pharmaceutically-acceptable acid-addition salts thereof.

3. an alkanolamine derivative as claimed in claim 1 selected from the group consisting of a compound of the formula given in claim 1 wherein $A^1$ is ethylene, 1-methylethylene or 1,1-dimethylethylene; wherein $A^2$ is a direct link or methylene, ethylidene or ethylene; wherein $R^1$ is 2-thienyl or 2-furyl; wherein either $R^2$ is hydrogen, chlorine, hydroxy, carbamoyl, cyano, methyl, allyl, methoxy or allyloxy and $R^3$ is hydrogen, or $R^2$ and $R^3$ together with the adjacent benzene ring form 1-naphthyl; wherein $X^1$ and $X^2$ are both —NHCO—; wherein $Y^1$ is a direct link and wherein $Y^2$ is a direct link or methylene, oxymethylene or methyleneoxy, or oxygen; and the non-toxic, pharmaceutically-acceptable salts thereof.

4. An alkanolamine derivative as claimed in claim 3 wherein $A^1$ is ethylene; wherein $A^2$ is methylene or ethylene; wherein $R^1$ is 2-thienyl or 2-furyl; wherein either $R^2$ is hydrogen, or chlorine, cyano, methyl, methoxy or allyloxy in the 2-position of the phenyl nucleus, and $R^3$ is hydrogen, or $R^2$ and $R^3$ together with the adjacent benzene ring form 1-naphthyl; wherein $X^1$ and $X^2$ are both —NHCO—; wherein $Y^1$ is a direct link and wherein $Y^2$ is a direct link or methylene; or a non-toxic pharmaceutically-acceptable acid-addition salt thereof.

5. An alkanolamine derivative as claimed in claim 1 wherein $A^1$ is ethylene, $A^2$ is a direct link or methylene or ethylene, $R^1$ is 2-thienyl or 2-furyl, either $R^2$ is hydrogen, chloro or cyano, or alkyl, alkenyl, alkoxy or alkenyloxy each of up to 3 carbon atoms and $R^3$ is hydrogen, or $R^2$ and $R^3$ together with the adjacent benzene ring form 1-naphthyl, $X^1$ and $X^2$ are both —NHCO—, $Y^1$ is a direct link and $Y^2$ is a direct link or methylene; or a non-toxic pharmaceutically-acceptable acid-addition salt thereof.

6. The compound:
1-(o-cyanophenoxy)-3-β-(2-thenamidoacetamido)ethylaminopropan-2-ol; or a non-toxic pharmaceutically-acceptable acid-addition salt thereof.

7. A non-toxic, pharmaceutically-acceptable acid-addition salt as claimed in claim 1 which is a hydrochloride, hydrobromide, phosphate, sulphate, oxalate, lactate, tartrate, acetate, salicylate, citrate, benzoate, β-naphthoate, adipate or 1,1-methylenebis-(2-hydroxy-3-naphthoate), or a salt derived from a sulphonated polystyrene resin.

8. The compound:
1-(o-chlorophenoxy)-3-β-2-thenamidoacetamido)ethylaminopropan-2-ol or a non-toxic pharmaceutically-acceptable acid-addition salt thereof.

* * * * *